United States Patent [19]

Simonsson et al.

[11] Patent Number: 4,748,116
[45] Date of Patent: May 31, 1988

[54] PEPTIDE SUBSTRATES FOR DETERMINATION OF PROTEASE ACTIVITY

[75] Inventors: Leif R. Simonsson, Hisings Backa; Salo Arielly, Kungsbacka; Leif E. Aurell, Särö ; Karl G. Claeson, Lindingö, all of Sweden

[73] Assignee: KabiVitrum AB, Stockholm, Sweden

[21] Appl. No.: 53,569

[22] Filed: May 21, 1987

Related U.S. Application Data

[63] Continuation of Ser. No. 294,127, Aug. 19, 1981, abandoned.

[30] Foreign Application Priority Data

Aug. 25, 1980 [SE] Sweden .................... 8005940

[51] Int. Cl.$^4$ .............. C12Q 1/38; C07K 5/06; C07K 5/08; C07K 5/10
[52] U.S. Cl. ..................... 435/23; 530/330; 530/331; 530/802
[58] Field of Search ............. 530/328, 329, 330, 331, 530/802; 435/23

[56] References Cited

U.S. PATENT DOCUMENTS

| | | | |
|---|---|---|---|
| 3,884,896 | 5/1975 | Blomback et al. | 260/112.5 R |
| 3,886,136 | 5/1975 | Claeson et al. | 260/112.5 R |
| 4,011,219 | 3/1977 | Nishii et al. | |
| 4,016,042 | 4/1977 | Svendsen | 260/112.5 R |
| 4,018,884 | 4/1977 | Cleeland, Jr. et al. | 260/112.5 R |
| 4,028,318 | 6/1977 | Aurell et al. | 260/112.5 R |
| 4,056,519 | 11/1977 | Bobbitt et al. | 260/112.5 R |
| 4,061,625 | 12/1977 | Af Ekenstam et al. | 260/112.5 R |
| 4,070,245 | 1/1978 | Svendsen | 260/112.5 R |
| 4,137,225 | 1/1979 | Af Ekenstam et al. | 260/112.5 R |
| 4,147,692 | 4/1979 | Nagatsu et al. | 260/112.5 R |
| 4,162,941 | 7/1979 | Aurell et al. | 260/112.5 R |
| 4,181,650 | 1/1980 | Maier, Jr. | 260/112.5 R |
| 4,207,232 | 6/1980 | Claeson et al. | 260/112.5 R |
| 4,216,142 | 8/1980 | Ali | 260/112.5 R |
| 4,217,269 | 8/1980 | Cole | 260/112.5 R |
| 4,221,706 | 9/1980 | Ali et al. | 260/112.5 R |
| 4,225,485 | 9/1980 | Buckler et al. | 260/112.5 R |
| 4,237,047 | 12/1980 | Sakakibara | 260/112.5 R |
| 4,242,329 | 12/1980 | Claeson et al. | 260/112.5 R |
| 4,244,865 | 1/1981 | Ali et al. | 260/112.5 R |
| 4,247,454 | 1/1981 | Af Ekenstam et al. | 260/112.5 R |
| 4,252,715 | 2/1981 | Aurell et al. | 260/112.5 R |
| 4,257,939 | 3/1981 | Sakakibara | 260/112.5 R |
| 4,257,940 | 3/1981 | Fujii et al. | 260/112.5 R |
| 4,259,233 | 3/1981 | Carrico et al. | 260/112.5 R |
| 4,260,682 | 4/1981 | Ryan et al. | 260/112.5 R |
| 4,261,893 | 4/1981 | Boguslaski et al. | 260/112.5 R |
| 4,275,153 | 6/1981 | Gargiulo et al. | 260/112.5 R |
| 4,276,375 | 6/1981 | Claeson et al. | 260/112.5 R |
| 4,276,378 | 6/1981 | Ryan et al. | 260/112.5 R |
| 4,278,763 | 7/1981 | Berger et al. | 260/112.5 R |
| 4,279,810 | 7/1981 | Claeson et al. | 260/112.5 R |
| 4,308,201 | 12/1981 | Fujii et al. | 260/112.5 R |
| 4,308,202 | 12/1981 | Fujii et al. | 260/112.5 R |
| 4,314,936 | 2/1982 | Yaron et al. | 260/112.5 R |
| 4,318,846 | 3/1982 | Khanna et al. | 260/112.5 R |
| 4,327,178 | 4/1982 | Ryan et al. | 260/112.5 R |
| 4,334,069 | 6/1982 | Buckler et al. | 260/112.5 R |
| 4,335,041 | 6/1982 | Ryan et al. | 260/112.5 R |
| 4,336,186 | 6/1982 | Gargiulo et al. | 260/112.5 R |
| 4,351,760 | 9/1982 | Khanna et al. | 260/112.5 R |

FOREIGN PATENT DOCUMENTS

| | | | |
|---|---|---|---|
| 2824917 | 2/1979 | Fed. Rep. of Germany . | |
| 2849708 | 5/1979 | Fed. Rep. of Germany . | |
| 7415229 | 6/1976 | Sweden | 260/112.5 R |

OTHER PUBLICATIONS

Chem. Abstr., vol. 85, (1976).
Clinical Chemistry, 25/4, 512–519, (1979).
Clinical Chemistry, 25/9, 1531–1546, (1979).

*Primary Examiner*—Delbert R. Phillips
*Attorney, Agent, or Firm*—Pollock, Vande Sande & Priddy

[57] ABSTRACT

Peptide sequences consisting of 2–4 amino acids with high affinity and comparatively high specificity to a number of various, physiologically important proteases are known to have been synthetized before. Such sequences with an added C-terminal marker have been widely used as substrates for the quantitative determination of the kind of proteases mentioned above. The method is based on the fact that the marker is split off under influence of the enzyme and that the liberated marker possesses an easily measurable, for instance, optic property which differs from that of the original substrate. The type of markers used until today have mainly been chromophores or fluorophores which can be quantified by photometry or fluorometry.

The present invention relates to a new type of markers coupled to known peptide sequences. These markers are luminol or isoluminol which in their free state can be brought to luminate intensely, but lose considerably in luminescence when they are amide-bound to a peptide sequence.

The peptide derivatives consist of acyl derivates of luminol (5-amino-2,3-dihydro-1,4-phthalazinedione) or isoluminol (6-amino-2,3-dihydro-1,4-phthalazinedione) where the acyl residue consists of an amide-bound amino acid or amino acid sequence with 2–4 amino acid residues and where the α-amino group is either free of acylated.

The greatest advantages of the luminogenic substrates according to the invention are that they are considerably more sensitive than the previously use chromogenic or fluorogenic substrates and can be used for measuring even extremely low protease concentration;

permit measurement of minute final volumes in standard luminometers which also are technically less complicated and, therefore, cheaper than both spectrophotometers and fluorometers; as a result, costs for both analysis reagents and devices can be cut down;

permit linear response measurements within a much wider concentration range than is the case with the usual chromogenic and fluorogenic methods;

generate markers less sensitive to deactivating interference as, for instance, chemical quenching; this distinguishes them from, for instance, fluorogenic substrates.

29 Claims, No Drawings

PEPTIDE SUBSTRATES FOR DETERMINATION OF PROTEASE ACTIVITY

This application is a continuation of Ser. No. 294,127, filed on Aug. 19, 1981, now abandoned.

TECHNICAL AREA

Protein-splitting enzymes, so-called proteases, have a number of vital functions in the human body. Trypsin and chymotrypsin are secreted from the pancreas and are active in the digestion process; elastases, kallikreins and cathepsins of various kinds, as well as the enzymes of the complement system, participate, among others, in reactions caused by inflammatory and allergic conditions; thrombin and factors IXa, Xa, XIa and XIIa are proteases in the chain of reactions leading to the formation of blood clots; endogeneous plasmin and exogeneous urokinase are proteases causing lysis of blood clots, etc.

An assay of the level of such proteases is of great importance in many situations. It makes possible the indirect assay of proenzyme levels by specific activation of such proenzyme, as well as the direct determination of the amount of active enzymes and also the level of their activators and inhibitors (as, for instance, plasminogen activators via plasmin, factor VIII via FX, heparin and antithrombin via Factor X or thrombin, $\alpha_2$-antiplasmin via plasmin, streptokinase via plasminogen, etc.).

Such assays are required, of course, in examinations of pathological conditions, but the determination of certain of these parameters is also of great importance in the preparations for surgical and medicinal treatment. Furthermore, the assay of protease activity is highly important and of great interest to biochemical research in view of the many physiological functions performed by proteases. Neither are the proteases concerned limited to only higher mammals. Proteases isolated from microorganisms are used in chemo-technical and food industry. One highly important method for the assay of endotoxin is based on the ability of endotoxin to activate a protein isolated from certain exotic crabs. The protease activity generated is proportional to the quantity of endotoxin (the so-called Limulus test).

BACKGROUND

The established procedure for quantitative assay of proteases is based either on immunological techniques or reaction with some kind of substrate—biological or synthetic.

Immunological methods utilizing the antibody-antigen reaction can, of course, be used with all proteases with available specific antibodies. There are, however, two important drawbacks—the method is time-consuming because the result does not appear till after 1-24 hours, and it is not sufficiently discriminative in so far as the protein—functionally active or not—reacts with its antibody as long as the antigenic structure (not determinant) is intact. Thus, the immunologically assayable quantity of a protein is equal to *or larger* than the quantity of functionally active protein. The advantage of the method, however, is its specificity and high sensitivity.

Examples of reactions with natural substrates used for protein determination are: the reaction of thrombin with fibrinogen in coagulation, the plasmin reaction with fibrin in fibrinolysis, and the elastase reaction with elastine. Thus, the usual diagnostic methods used in the field of coagulation are mostly based on the fact that plasma samples are activated under standardized conditions and the final reaction step is the reaction of thrombin with fibrinogen. In this procedure, fibrinogen is transferred to insoluble fibrin, the forming of which is the final step of the assay. Another example is the horseshoe crab haemocytelysate which coagulates after endotoxin activation of its clotting enzyme (Limulus test for endotoxin).

Other methods for the determination of proteases use biological proteins which are not in themselves natural substrates for the protease in question. Examples: casein, haemoglobin, gelatine and insulin.

The disadvantage of working with protein substrates is the usually very limited sensitivity and lack of specificity of these methods. Further, they are difficult to standardize, are rather time-consuming and cannot easily be automatized.

Synthetic, low-molecular weight substrates based on amino acids or short peptides provided with a marker easily determinable and easily split by protease have, in recent years, considerably facilitated the methods for quantification of proteases by eliminating several of the above-mentioned disadvantages.

These substrates—being organic synthetic chemicals—have in common the quality of being easily standardized. Further, there is the possibility of making these substrates more or less specific for various types of proteases by a tactical choice of the amino acid or amino acid sequence linked to the marker. Thus, the choice of a suitable substrate structure can be adapted to the actual demand. In addition, these kinds of substrates permit the use of markers to be liberated in the protease reaction and, thus, easily quantified in an objective measuring equipment (spectrophotometer, fluorimeter, radioactivity counter).

Two types of derivatives have been utilized as substrates, esters or amide derivatives of the markers. As a rule, the ester substrates have proved to be more easily split than the corresponding amide derivatives. At the same time, however, splitting of amide derivatives is a physiologically and biochemically better model of the specific function of proteases which is splitting of amide bindings. In addition, the ability of a protease to split esters and amides is in certain cases related to different reaction centers within the molecule which means that, in such a case, amide substrates are required in order to be able to determine the physiological function.

Among the markers used in synthetic substrates of the amide type according to the foregoing, derivatives of p-nitroaniline (pNA) for photometric quantification and of $\beta$-naphthylamin ($\beta$NA) as well as of 2-amino-4-methylcoumarin (MCA) for fluorometric quantification are the most commonly used and described, according to information available from the literature and accessible patent documents.

Substrates with radioactive labelled markers are sporadically mentioned in the literature but, as the properties of an intact substrate and a split-off marker do not differ in regard to radioactivity, a separation step is required before the assay. This complication, in addition to the risk involved in the handling of radioactive material and the problem of lack of stability of the substrate due to the natural decompositions of the radioactive isotope introduced in the substrate, has made this kind of substrate useful only in very special instances.

Comprehensive studies have been carried out with synthetic substrates—usually provided with pNA or MCA markers—in order to establish structures which, with a limited number of amino acids in the peptide part (usually 2 to 4), provide an optimum of sensitivity and specificity for a number of endo- and exogenic proteases important from the clinical point of view. It has been found that the pNA- or MCA marker, respectively, is of no decisive significance to the general properties of the substrates. Thus, the specificity profile of a substrate, that is, its relative reactivity to various enzymes, is mainly governed by the peptide structure. Further, the differences in $K_m$ and $k_{cat}$-values do not give differences in substrate turnover rate in terms of "moles substrate converted per time unit" larger than usually about 10 times. If, furthermore, the solubility of each substrate allows for substrate concentrations stronger than twice the $K_m$-concentration, only $k_{cat}$ is essential. The differences mentioned in the literature may, in certain cases, also be explained by different buffer systems and contents of organic solvents.

Thus, the capacity of each substrate for assaying low levels or small amounts of a certain enzyme is primarily determined by the possibility to determine low levels or small volumes of each marker after its release from the substrate.

The smallest content of MCA in pure aqueous solutions which can be determined photometrically or fluorimetrically would be $10^{-6}M$ or $10^{-9}M$ respectively. But as also intact substrate in considerably higher concentrations is present in the solution in protease assays with chromogenic and fluorogenic synthetic substrates, the sensitivity of the methods is limited by the background effect supplied by unsplit substrate—in particular when minute concentrations of released marker are to be determined.

This difference is due to the fact that the properties of the marker are not the same when it is free and when it is acylated by an amino acid or a peptide. Whichever amino acid or peptide forms the acyl group is of minor imporance. Thus, the difference between an MCA substrate and free MCA is 500 to 700 that is the fluorimeter reading is the same for $1,5—2\cdot10^{-7}M$ MCA as for a $1\cdot10^{-4}M$ MCA substrate solution (Zimmermann et al., Anal Biochem 70, 258 (1976), ibid. 78, 47 (1977), Proc Natl Acad Sci USA 75, 750 (1978). The linear response is said to be obtained for a 500-fold concentration range.

The smallest determinable volume depends on the type of appliance used but usually a volume of 0.5 to 3 ml is required for these photo- and fluorometric methods—volumes of less than 0.5 ml require special equipment for exact determination because both types of marker require a certain amount of radiation to give an exact measure of the light quantity absorbed or emitted.

DESCRIPTION OF THE INVENTION

The present invention relates to a new type of marker for the determination of protease activity. It is based on the fact known per se that compunds of the cyclic diacylhydrazide type

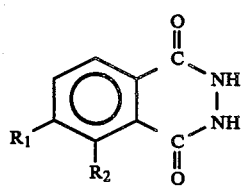

$R_1 = H, R_2 = NH_2 \longrightarrow$ luminol (5-amino-2,3-dihydrophthalazin-1,4-dion)

$R_1 = NH_2, R_2 = H \longrightarrow$ isoluminol (6-amino-2,3-dihydrophthalazin-1,4-dion)

can be brought to emit light by addition of an oxidizer. This is the phenomenon known as chemiluminescence (CL). The special case when the reaction is being catalyzed by an enzyme is referred to as bioluminescence (BL). Analytical techniques such as photometry and fluorometry are based on the changes caused by the samples on the incoming light. CL uses chemical reactions causing excited conditions in one or more of the reactants, recess to the ground state being followed by emission of light. In other words, chemiluminescence is an emission process while photometry and fluorometry are based on the absorption process. A summary on the subject relating to its application in analytical biochemistry is given in Methods in Enzymology, Vol. 57, ed. deLuca, Acad Press, New York 1978, and relating to its use in clinical chemistry in Whitehead et al., Clin. Chem 25, 1531 (1979), and Gorus & Schram, ibid. 25, 512 (1979).

A number of analytical applications utilizing luminescent reactions have been documented. They are based on the principle that either one of the reactants in the oxidation reaction appears in a concentration so small that its level determines the speed and thus becomes determinable (e.g. ATP, NADH (BL) and $H_2O_2$ (CL)), or that the substance to be determined consumes or produces or in some other way is linked to the reactants of the oxidation system to the effect that its concentration indirectly limits the reaction process (e.g. ADK, kreatine phosphate via ATP, malate and FMN via NADH, as well as glucose and haemoglobin via $H_2O_2$). Further, BL and CL have been used for immunoassays, both direct by binding, for instance, luminol or isoluminol to an antibody or antigen as a marker, or by using a BL catalysing enzyme or other co-factor in the same way.

The present invention is based partly on the observations described in the experimental part, namely that acylated and non-acylated derivatives of isoluminol and luminol have quite different properties as regards the capacity of emitting light under standard conditions for the oxidation reaction, partly on the fact that—if the acyl group consists of an amino acid or a peptide, or a derivative of either—proteolytic enzymes can split such compounds to the effect that isoluminol or luminol is released and can be measured by addition of excess of the other reactants of the oxidation reaction. Thus, utilizing the fact known per se that amino acid derivatives and peptide derivatives containing 2 to 4 tactically chosen amino acid residues have high affinity to a number of important and well characterized proteases, the present invention shows a new type of substrates for the determination of the abovementioned type of proteases. These substrates allow the quantification of very low concentrations and small volumes in equipment technically less complicated then spectrophotometers and fluorimeters.

Due to the fact that such parameters as
type of buffer system, reaction time
reaction temperature,
substrate concentration,
enzyme purity, etc.
all influence the definition of the lowest protease activity (unit or quantity per test volume) assayable with a certain method, the sensitivity limit of the different methods is here defined by the quantity of free marker assayable in the presence of a certain concentration of intact substrate. All such concentration values refer to the substrate-enzyme solution.

Depending on the dilution factor and type of oxidation step, isoluminol and luminol in "pure" systems are assayable down to the concentration $3-10\cdot10^{-10}$ and $10^{-11}-10^{-10}$M respectively. Due to the fact that the substrates according to the present invention show unexpected great difference in their light emission capacity as compared with corresponding concentrations of free marker (usually 2,500-10,000) isoluminol, for instance, is assayable in concentrations as low as $1\cdot10^{-9}$M. There is linearity up to $10^{-5}$M and, thus, the assay area covers a $10^4$-fold concentration range. The analyses only require 10 to 15 $\mu$l volume of a substrate-enzyme solution.

The advantages of the compounds according to the invention are the fact that, as distinguished from the MCA-marked fluorogenic substrates which today are considered as being highly sensitive, the compounds according to the invention permit the determination of a change in concentration of $1\cdot10^{-9}$M of free marker in the presence of $1\cdot10^{-4}$M substrate, compared with $1\cdot10^{-7}$ MCA and $1\cdot10^{-6}$ pNA which fact known per se means considerably increased sensitivity in the assay of extremely low protease concentration with synthetic substrates;

the fact that these compounds permit assays within a much wider concentration range: 1,000 to 10,000 times for isoluminol, 500 to 700 times for MCA and 100 times for pNA of free marker in the same appliance merely by choosing a suitable area of sensitivity;

the fact that these compounds—as distinguished from very easily split ester substrates—are amides and thus reflect the catalytic function of the enzyme more truly than is the case with an ester substrate. At the same time, they are chemically more stable in neutral or slightly basic environments than are ester substrates of the type p-nitrophenylester or umbelliferone;

the fact that these compounds as distinguished from radioactive labelled substrates which today are considered as being highly sensitive have the advantage not only of the absence of radioactivity and spontaneous decomposition but also permit assays of the reaction solution without previous separation step for the isolation of the reaction products;

the fact that these compounds as distinguished from chromophore and fluorophore-marked substrates which are in common use to-day permit determinations of minute quantities of substrate-enzyme solution—of the size 10 to 50 $\mu$l—in standard appliances for luminescence assays which latter also are technically less complicated and thus less expensive than spectrophotometers and fluorimeter—all taken together resulting in lower costs for analyses with regard both to reagent and appliance;

the fact that, as distinguished from, for instance, flurorogenic compounds, the compounds according to the invention generate markers less sensitive to deactivating interference such as chemical quenching which, among other things, is achieved by a dilution step preceding the oxidation step.

EXPERIMENTAL PART

I. General Specification

When using substrates according to the invention, the commonly used buffer systems for enzyme-substrate reactions can be applied as, for instance, tris, trisimidazole, phosphate, barbiturate, veronal or glycine buffer, with suitable addition of base or acid and inorganic salts for obtaining best possible conditions with regard to pH and ionic strength for the reaction of enzyme with substrate.

Following the selected reaction time which usually is 0.5 to 10 minutes, the reaction is discontinued either in all of the enzyme-substrate solution or in part of the same by adding base or acid to obtain a change in pH effective enough to stop the enzymatic hydrolysis of the substrate.

Then the quantity of released CL-marker (luminol or isoluminol) is determined by adding a suitable oxidizer and measuring the thus emitted amount of light in a suitable appliance. Due to the fact that the amount of released marker is in linear proportion to the amount of enzyme, and the the light quantity emitted is in linear proportion to the amount of CL-marker, the light quantity constitutes the measure of protease quantity (protease activity).

Adequate oxidation system are, for instance, aqueous solution of hydrogenperoxide ($H_2O_2$) in the presence of a catalyst or oxidation promoting compound, such as various kinds of peroxidases, catalases and other biological compounds which are derivatives of the haemo group, for instance, microperoxidase, hematin, several metal ions, for instance, $Cu^{2+}$, $Co^{2+}$, $Cr^{3+}$, $Fe^{2+}$, ferric cyanide (($K_3Fe(CN)_6$).

hypochlorite, persulphate, permanganate, periodate, perborate, oxygen in the presence of suitable catalysts, superoxides ($KO_2$) if the reaction determination is made in an anhydric system.

Hydrogenperoxide plus hematin as well as hydrogenperoxide plus microperoxidase or catalase have proved to be particularly well suited as oxidation systems for the determination of CL-marker from the substrates of the present invention.

The light emission is pH dependent. Thus, the reactions with hematin should be performed at a pH of 10 to 13, and reactions with microperoxidase at pH 8 to 13 to obtain the best possible results.

The substrate-enzyme reaction solution only being a limited portion of the CL determination reaction solution each reaction can be performed at its most favourable pH value.

Substrates according to the present invention can be used with commercially available luminescence meters (for instance, LKB Luminometer 1250, Aminco Chem-Glow Photometer) and also in equipment specially made for the purpose, as long as this equipment comprises a light detector (photomultiplier tube or photosensitive diode), amplifier and signal converter, signal recorder unit (analogue or digital "display", printer or recorder) as well as a completely dark reaction chamber with facilities for direct test injection.

The speed of CL reactions varies. In the case of oxidation of isoluminol or luminol with $H_2O_2$ and catalyst or an oxidation promoting compound, light emission is a very rapid and rather short-lived reaction which, in practice, starts at the moment when the last reagent is placed in the reaction vessel, that is, less than 2 seconds after that addition. The quantity of light is obtained either by integration of the light intensity over a certain time interval or—when the process exceeds as fast as mentioned in the example above—simply by measuring the peak height of the recorded signal.

By comparison of the quantity of light emitted with that obtained from samples of marker with known concentrations—possibly making adjustments on account of additional light intensity due to background emission from, for instance, intact substrate and the components of the oxidation system—the molar quantity of marker released per time and enzyme unit can be determined, as well as kinetic parameters. The enzyme concentration of an unknown sample is best determined by comparison with a standard graph obtained by using known enzyme concentrations under equal conditions.

In the synthesis of substrates according to the invention, traditional methods well-known in peptide chemistry are adapted. The synthetizing procedure is, however, facilitated if the luminol and isoluminol in the acylation reactions are introduced as 3- and 4-amino-N-methylphthalimide (ANMP), respectively, in particular when the first (C-terminal) amino acid is to be coupled. By conversion of the acyl derivatives thus obtained of 3- or 4-ANMP with hydrazine hydrate in ethanol or dimethylformamide, it is transferred to the corrsponding luminol and isoluminol derivatives, respectively.

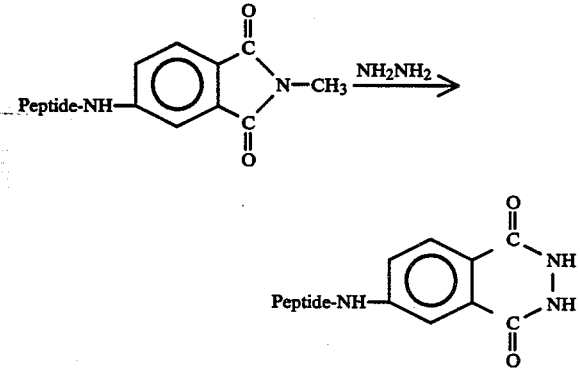

It appears then that ANMP-derivatives are stable against the commonly used deprotection and coupling reactions and that hydrazinolysis can take place without detriment to any components of the amino acid or peptide structure. This is illustrated by the experiments described in the following.

For condensation of ANMP and a properly protected amino acid, adequate coupling methods are the ones commonly used for the corresponding condensation of anilin and anilin derivatives with amino acids and peptides as, for instance, the so-called phosphaza method, mixed anhydride method, or the use of a coupling agent such as EEDQ (N-ethoxy-carbonyl-2-ethoxy-1,2-dihydroquinoline), or DCCI, possibly in the presence of an activating alcohol such as N-hydroxysuccinimide or N-hydroxybenzotriazole.

The principle of synthetizing peptide derivatives according to the invention may be a step-wise addition of amino acids to the C-terminal amino acid residue, either initially linked to the CL-marker or ANMP or furnished with a removable carboxyl protection group in which case ANMP is subsequently coupled to the protected peptide derivative. Alternatively, the N-terminal peptide may be synthesized separately and then linked to the C-terminal amino acid residue having a CL-marker, ANMP or a removable carboxyl protecting group coupled to it as described in the foregoing.

Whichever principle is chosen, purification of the intermediate and end products by gel filtration chromatography is most suitable because this method warrants rapid synthesis and maximal yields.

As an amino protecting group, the carbobenzoxy- or t-butyloxycarbonyl group or related groups, such as the p-methoxy, p-nitro or p-methoxyphenylazocarbobenzoxy group, are recommended.

For protection of the guanidino group of the arginine, the use of protonisation, the nitro group or the p-toluenesulphonyl group have proved to be adequate.

The hydroxyl group of tyrosine, serine and threonine is adequately protected by the t-butyl or benzyl group. Methyl-, ethyl- or benzylester is an adequate removable carboxyl protecting group.

The coupling of two amino acids or a peptide fragment and an amino acid is obtained by activating the α-carboxyl group. The activated derivative may either be isolated or generated in situ and may be, for instance, p-nitrophenyl, trichlorophenyl, pentachlorophenyl, pentafluorophenyl, N-hydroxybenzotriazole or N-hydroxysuccinimido ester, symmetric or assymetric anhydride or azide. The usual coupling agents for direct coupling or generating the mentioned esters are dicyclohexylcarbodiimide, N-ethoxycarbonyl-2-ethoxy-1,2-dihydroquinoline or their equivalents.

The protecting groups are completely or partly removed by a tactical choice of protecting groups and deprotecting methods. For example: The carbobenzoxy group is split off with hydrogen bromide in acetic acid, and the t-butyloxy group with trifluoro acetic acid. Esters are hydrolysed with sodium hydroxide solution. For complete deprotecting, hydrofluoric acid and, sometimes, hydrogen gas in the presence of a catalyst, are suitable reagents.

A suitable method for purifying intermediate or end products is not only crystallization, but also gel filtration chromatography on cross-linked dextran gels of the type Sephadex ® as a solid phase. Sephadex ® is to be used with either aqueous solutions (G-15 or G-25) with an addition of 5 to 30% acetic acid, or with alcohol solutions—preferably methanol—(LH-20), or for ion exchange chromatography in mixtures of alcohol and water (QAE-A-25).

Reaction solutions, intermediate products, eluates from column chromatography as well as end products obtained in solid form by lyophilization from water or water and acetic acid, or alcohol, are checked by thin-layer chromatography. Here, pre-fabricated glass plates, with silica gel $F_{254}$ (Merck) as an absorption medium, are used.

The solvent systems used are:
$P_1 CHCl_3$, MeOH: 9:1 (volume)
$P_a CHCl_3$, MeOH, AcOH: 17:2:2
$P_{a6} CHCl_3$, MeOH, AcOH, $H_2O$: 34:4:9:2
A n-BuOH, AcOH, $H_2O$: 3:1:1
M n-BuOH, AcOH, pyridine, $H_2O$: 15:3:10:12
$M_3$ EtOAc, AcOH, pyridine, $H_2O$: 30:60:20:11

Following chromatography, the plate is inspected in UV light (254 nm) and then developed with ninhydrine and with a chlorine/dicarboxidine reagent according to normal procedure. All end products are homogeneous according to TLC performed on a quantity of 50–100 μg. The given $R_f$ values are the results of single runs.

An amino acid analysis of the end product shows that in all cases these products contain the expected amino acids, and the relative contents of the respective amino acid residue lie within ±5% of the expected values.

The optical activity of the end product is determined at 589 nm in 50% acetic acid at a concentration of 0.2 to 1.0 g/100 ml (c=0.2 to 1.0).

The homogeneity of the end product is also checked by high performance liquid chromatography using $C_{18}$-derived silica gel as a solid phase and 40% methanol in 0.1M sodium acetate, pH 4.6, as an eluant, and UV light at 254 nm as a detection method. This method also provides a check that no free marker pollutes the end product.

The following experimental data show that luminol and isoluminol are generally applicable as markers of protease substrates.

II. Synthesis

Peptide synthesis distinguishes itself by the fact that a number of standard reactions may be used independently of amino acid structure and peptide size and, therefore, these standard reactions are described in the following while the synthetized compounds are listed in the table with reference made to the described reactions.

Abbreviations (Unless otherwise stated, all amino acids have the L-configuration.)

| | | | | |
|---|---|---|---|---|
| Arg | = Arginine | Leu | = | Leucine |
| Phe | = Phenyl alanine | Tyr | = | Tyrosine |
| Pip | = Pipecolinic acid | pGlu | = | Pyroglutamic acid |
| Pro | = Proline | Glu | = | Glutamic acid |
| Val | = Valine | Ser | = | Serine |
| Ala | = Alanine | Gly | = | Glycine |
| Ile | = Isoleucine | Lys | = | Lysine |
| AcOH | = Acetic acid | HOBt | = | N—Hydroxy-benzotriazole |
| TFA | = Trifluoro acetic acid | DCCI | = | Dicyclohexyl-carbodiimide |
| Boc— | = t-Butyloxy-carbonyl | Lum | = | Luminol |
| Cbo— | = Carbobenzoxy | Isl | = | Isoluminol |
| DMF | = Dimethyl formamide | Bzl— | = | Benzyl |
| Et3N | = Triethylamine | Bz— | = | Benzoyl |
| EtOAc | = Ethyl acetate | Glt | = | Glutaryl |
| EtOH | = Ethanol | Tos— | = | p-Toluene-sulphonyl |
| MeOH | = Methanol | Ac— | = | Acetyl |
| n-BuOH | = n-Butanol | Suc— | = | Succinyl |
| ANMP | = Amino-N—methyl-phthalimide | | | |
| HOSu | = N—Hydroxy-succinimide | | | |
| TLC | = Thin Layer Chromatography | | | |
| GPC | = Gel Permeation Chromatography | | | |
| HPCL | = High Performance Liquid Chromatography | | | |
| I | = Ionic strength | | | |

Reaction type A

Coupling of 3- or 4-ANMP 30 mmol of 3- or 4-AMNP (5.28 g) is suspended in 100 ml of anhydrous pyridine, and 1.4 ml $PCl_3$ dissolved in 20 ml of pyridine is added dropwise at 0° C. while the mixture is being stirred. After 30–45 minutes at room temperature, 30 mmol of amino-protected amino acid or peptide is added. When the solution has cleared (usually after 24 to 72 hours), the completeness of the reaction is checked by TLC. Evaporation and processing by acid and basic washings produce an oily residue which can be crystallized from EtOH or MeOH, possible after an addition of water. Yield: 70 to 85%.

Reaction type B

Removal of Cbo—, Boc and Bzl—O— groups 10 mmol of the thoroughly dried Cbo-derivative is suspended in 25 ml of dry AcOH, and 15 ml 5.6N HBr is added under moisture free conditions at room temperature.

After reacting for 45–60 minutes, the solution is poured into 300 ml of dry ether while it is being stirred vigourously. The ether solution is sucked off the resulting precipitate which is then washed with 2 to 3 portions of 100 ml ether each. The thus obtained hydrobromide of $N^\alpha$-deblocked compound is dried over NaOH pellets in vacuo at 40° C. for 3 to 16 hours.

Reaction type C

Removal of Boc group 10 mmol of the thoroughly dried Boc derivative is dissolved in 200 ml of 25% TFA in $CH_2Cl_2$ under moisturefree conditions at room temperature. After reacting for 20 minutes, the solution is poured into 500 ml of dry ether. After filtering, the resulting precipitate is washed with large quantities of ether. The thus obtained trifluoro acetate of $N^\alpha$-deblocked compound is dried over NaOH pellets in vacuo at 30° C. for 2 to 3 hours.

Reaction types D, E and F

Coupling reactions

Releasing α-amino group

For acylation of the derivatives obtained according to reaction type B or C, the α-amino group must be present as a free base. This may be effected in various ways. For instance, an equivalent amount of tertiary amine (for instance, Et₃N or N-ethyl morpholine) may be added to a DMF solution of the HBr or TFA derivative cooled to −10° C. In the case of Et₃N. HBr derivatives, the precipitated Et₃N. HBr is filtered off. Alternatively, the HBr or TFA derivative may be dissolved in 5% aqueous sodium bicarbonate from which the liberated derivative is extracted into, for instance, EtOAc or butanol; the organic phase is then dried and evaporated.

D with an $N^\alpha$-protected, active ester derivative.

11 mol of $N^\alpha$-protected p-nitrophenyl or N-hydroxysuccinimide ester derivative of the amino acid or peptide to be coupled is added, at −10° C., to a solution of 10 mmol of peptide or amino acid derivative, obtained according to the foregoing, in 20 to 50 ml of freshly distilled DMF. After reacting for 1 hour at −10° C., the solution is buffered with 5 mmol of tertiary amine and allowed slowly to attain room temperature. The reaction process can be followed by TLC analyses. If required, another 5 mmol of base is added after repeated cooling. When the reaction is finished, the solution is evaporated to produce an oily residue which is stirred with some portions of water. The rest is purified by GPC or recrystallization. If GPC is used for purification of the coupling product and the latter has an eluation volume fully or partly equivalent to that of of the active ester derivative, contamination of the coupling product may be prevented by conversion—after finished reaction but before evaporation—of unconsumed active ester derivative with an excess of 3 to 5 mmol of primary amine, for instance, n-butylamine, for 30 minutes at room temperature. This is followed by processing as in the foregoing.

E with N-protected amino acid or peptide and generating active ester in situ.

At $-10°$ C., 11 mmol of $N^\alpha$-protected amino acid, or equivalently protected peptide derivative with a C-terminally free carboxyl group, 11 mmol HOBt or HOSu and 11 mmol of DCCI are added to a solution of 10 mmol of peptide or amino acid derivative, obtained according to the foregoing, in 20 to 50 ml freshly distilled DMF. After 1 to 30 hours at $-10°$ C., the reaction solution is allowed to attain room temperature. The reaction process can be followed by TLC analyses. After reaction, the solution is poured into 100 to 300 ml of 5% NaHCO$_3$ (aq.) while being stirred, or evaporated to an oily residue which is stirred with some portions of sodium bicarbonate.

The resulting precipitate is washed in water after filtration or pouring off the solvent. It is then purified by GPC or recrystallization.

F with anhydride (F1) or acid chloride (F2).

N-terminal acyl groups are introduced by reacting the amino acid or peptide derivatives obtained according to the foregoing with the anhydride of the corresponding acyl group (for instance, succinyl, glutaryl, benzoyl or acetyl) or the acid chloride of the acyl group (for instance, benzoyl, acetyl or tosyl). Procedure as described in D and E above with regard both to solvents and amounts and to reaction temperature and processing.

Reaction type G

Catalytic hydrogenation for removal of Cbo, benzyl—O and NO$_2$ groups 5 mmol of peptide is dissolved or suspended in 15 to 50 ml of solvent which may be MeOH, AcOH or mixtures of these, possibly with an addition of 1.2 equivalents of HCl. Then the catalyst, 10% palladium on carbon (Pd/C), is added. Hydrogen gas is introduced and the reaction allowed to continue at room temperature while being stirred until no more hydrogen gas is consumed. (2 to 24 hours.) The catalyst is filtered off, the purity checked by TLC and the desired product isolated either directly by evaporation and perhaps lyophilization, or after GPC. If the derivative is to be used for further acylation reactions with DCCI, compounds existing as acid addition salts of AcOH must be converted to the corresponding HCl salt by GPC ion exchange.

Reaction type H

Removal of all remaining protecting groups 0,2 to 1.0 mmol of the fully or partly protected amino acid or peptide derivative is deprotected by being reacted for 60 minutes at 0° C. with 5 to 20 ml of dry HF in the presence of 0.2 to 1.0 ml of anisole in equipment built for this purpose according to Sakakibara.

After reaction and complete distillation of all HF, the crude product is dissolved in 10–30% AcOH in water and possibly shaken with a small amount of ether and purified by GPC. The product is isolated by lyophilization from diluted AcOH. It may also be isolated by dissolving in MeOH and precipitating in ether the product remaining after the distillation of HF. After filtration, the product is dried in the usual way and used direct in the next reaction step or purified by GPC.

Reaction type I

Conversion of 3- or 4-ANMP derivatives to luminol or isoluminol derivatives by hydrazinolysis 2 mmol of peptide is dissolved in 15 ml of DMF and then 1.0 NH$_2$NH$_2$.H$_2$O (hydrazine hydrate) is added and stirred at initially 0° C. and then room temperature. The reaction solution is evaporated after 3 to 4 hours and the rest purified by GPC.

Instead of using the above method which is described here for the first time, the reaction can be effected in EtOH and accelerated by reflux boiling for about 30 minutes. The product is isolated by evaporation and GPC.

Gel filtration chromatography

With GPC of protected peptide or amino acid derivatives, crude products or evaporated mother liquors obtained after crystallization, simplified processing and optimum yields are obtained. The substance is dissolved in MeOH and applied to a suitably sized column (volume 0.5 to 7.5 l, length 100 cm) packed with Sephadex ®LH-20 with MeOH and eluated with the same solvent. The eluate is fractionated into convenient volumes, and its UV absorption (254 nm) is continually determined. Fractions containing the product are checked for purity by TLC and the pure products are collected and evaporated.

To purify fully or partly deprotected amino acid and peptide derivatives, an acetic acid solution of the crude product is moved to a suitably sized column (volume 0.5 to 2.0 l, length 60 cm) packed with Sephadex ®G-15 swollen in 10 to 30% AcOH (aq) and eluated with the same solvent. Following the procedure described in the foregoing, the pure product-containing fractions are lyophilized, possibly after some evaporation at 20° C. For ion exchange and any required additional purification of a previously chromatographed product, a column with a slightly basic ion exchanger, Sephadex ® QAE-25 in chloride form, swollen in MeOH:water 95:5 with the same medium as a solvent and eluant can be used. The pure product is lyophilized from water after evaporation.

TABLE

| End prod. | Intermediary prod. | Formula | Starting material | Synthesis | Yield | TLC system R$_f$ | (α) |
|---|---|---|---|---|---|---|---|
| I | | H—D-Ile—Pro—Arg—Isl.2 HCl | 1e | C | ⎫ | A:0.25 | −98.3° |
| | 1e | Boc—D-Ile—Pro—Arg—Isl.HCl | 1d | I | ⎬ 25 | A:0.57 | |
| | 1d | Boc—D-Ile—Pro—Arg—4-ANMP.HCl | 1c | E | ⎭ | A:0.59 | |
| | 1c | H—Pro—Arg—4-ANMP.2 HCl | 1b | H | 86 | A:0.14 | |

TABLE-continued

| End prod. | Intermediary prod. | Formula | Starting material | Synthesis | Yield | TLC system R_f | (α) |
|---|---|---|---|---|---|---|---|
|  | 1b | Cbo—Pro—Arg(NO₂)—4-ANMP | 1a | B/E | 85 | P₁:0.32 |  |
|  | 1a | Cbo—Arg(NO₂)—4-ANMP |  | A | 72 | P₁:0.37 |  |
| II |  | Boc—Val—Pro—Arg—Isl.HCl | 2a | D | 32 | A:0.47 | −101.9° |
|  | 2a | H—Pro—Arg—Isl.2 AcOH | 1c | I | 60 | M₃:0.18 |  |
| III |  | Boc—Leu—Gly—Arg—Isl.HCl | 3c | I | 54 | A:0.47 | −44.6° |
|  | 3c | Boc—Leu—Gly—Arg—4-ANMP | 3b | G | 90 | A:0.47 |  |
|  | 3b | Boc—Leu—Gly—Arg(NO₂)—4-ANMP | 3a | B/D | 53 | P₁:0.12 |  |
|  | 3a | Cbo—Gly—Arg(NO₂)—4-ANMP | 1a | B/D | 70 | P₁:0.21 |  |
| IV |  | Boc—Val—Leu—Gly—Arg—Isl.HCl | 4b | I | 28 | A:0.50 | −50.5° |
|  | 4b | Boc—Val—Leu—Gly—Arg—4-ANMP.AcOH | 4a | G | 90 | A:0.47 |  |
|  | 4a | Boc—Val—Leu—Gly—Arg(NO₂)—4-ANMP | 3b | C/E | 73 | Pa:0.37 |  |
| V |  | H—D-Val—Leu—Arg—Isl.2 HCl | 5d | C |  | A:0.33 | −62.4° |
|  | 5d | Boc—D-Val—Leu—Arg—Isl.HCl | 5c | I |  | Pa₆:0.29 |  |
|  | 5c | Boc—D-Val—Leu—Arg—4-ANMP | 5b | G | 29 | Pa₆:0.55 |  |
|  | 5b | Boc—D-Val—Leu—Arg(NO₂)—4-ANMP | 5a | B/E |  | P₁:0.29 |  |
|  | 5a | Cbo—Leu—Arg(NO₂)—4-ANMP | 1a | B/D | 88 | P₁:0.32 |  |
| VI |  | pGlu—Gly—Arg—Isl.HCl | 6b | I |  | A:0.20 | −46.1° |
|  | 6b | pGlu—Gly—Arg—4-ANMP.AcOH | 6a | G | 48 | A:0.24 |  |
|  | 6a | Cbo—pGlu—Gly—Arg(NO₂)—4-ANMP | 3a | B/E |  | Pa:0.08 |  |
| VII |  | Cbo—Gly—Pro—Arg—Isl.HCl | 7a | I |  | A:0.36 | −49.9° |
|  | 7a | Cbo—Gly—Pro—Arg—4-ANMP.AcOH | 1b | B/D | 4 | A:0.37 |  |
| VIII |  | Boc—Ile—Glu(NC₅H₁₀)—Gly—Arg—Isl.HCl | 8b | I |  | A:0.45 | −39.6° |
|  | 8b | Boc—Ile—Glu(γ-pip)—Gly—Arg—4-ANMP | 8a | E | 26 |  |  |
|  | 8a | 2 AcOH.H—Arg—4-ANMP | 1a | H | 98 | M:0.45 |  |
| IX |  | pNO₂—Cbo—Phe—Pro—Arg—Isl.HCl | 2a | B/D | 80 | A:0.50 | −74.2° |
| X |  | Cbo—Phe—Pro—Arg—Isl.HCl | 2a | B/D | 30 | A:0.53 | −72.8° |
| XI |  | Boc—Phe—Pro—Arg—Isl.HCl | 2a | BD | 55 | A:0.52 | −76.5° |
| XII |  | H—Phe—Pro—Arg—Isl.2 HCl | XI | C | 49 | A:0.26 | −48.8° |
| XIII |  | Bz—Arg—Lum.HCl | 13c | I | 93 | A:0.49 | +6.0° |
|  | 13c | Bz—Arg—3-ANMP.AcOH | 13b | H | 75 | A:0.49 |  |
|  | 13b | Bz—Arg(NO₂)—3-ANMP | 13a | B/Fl | 85 | P₁:0.30 |  |
|  | 13a | Cbo—Arg(NO₂)—3-ANMP |  | A | 31 | A:0.77 |  |
| XIV |  | pNO₂—Bz—Arg—Isl.HCl | 14b | I | 61 | A:0.47 | +21.2° |
|  | 14b | pNO₂—Bz—Arg—4-ANMP.AcOH | 14a | H | 42 | A:0.50 |  |
|  | 14a | pNO₂—Bz—Arg(NO₂)—4-ANMP | 1a | B/D | 97 | P₁:0.17 |  |
| XV |  | Bz—Arg—Isl.HCl | 15b | I | 79 | A:0.45 | +4.1° |
|  | 15b | Bz—Arg—4-ANMP.AcOH | 15a | H | 69 | A:0.47 |  |
|  | 15a | Bz—Arg(NO₂)—4-ANMP | 1a | B/Fl | 82 | P₁:0.22 |  |
| XVI |  | Cbo—Phe—Arg—Isl.AcOH | 16a | I | 36 | Pa₆:0.22 | −19.3° |
|  | 16a | Cbo—Phe—Arg—4-ANMP.AcOH | 8a | D | 74 | Pa₆:0.5 |  |
| XVII |  | Boc—Pro—Phe—Arg—Isl.HCl | 17a | I | 30 | Pa₆:0.24 | −58.4° |
|  | 17a | Boc—Pro—Phe—Arg—4-ANMP.AcOH | 8a | E | 73 | Pa₆:0.32 |  |
| XVIII |  | H—Gly—Pro—Lys—Isl.2 HCl | 18d | B | 70 | M₃:0.25 | −99.5° |
|  | 18c | Boc—Gly—Pro—Lys(Cbo)—Isl | 18c | I | 50 | Pa₆:0.72 |  |
|  | 18c | Boc—Gly—Pro—Lys(Cbo)—4-ANMP | 18b | C/E | 80 | P₁:0.58 |  |
|  | 18b | Boc—Pro—Lys(Cbo)—4-ANMP | 18a | C/E | 84 | P₁:0.69 |  |
|  | 18a | Boc—Lys(Cbo)—4-ANMP |  | A |  | P₁:0.63 |  |
| XIX |  | H—Val—Leu—Lys—Isl.2 HCl | 19c | B | 59 | M₃:0.60 | −42.9° |
|  | 19c | Boc—Val—Leu—Lys(Cbo)—Isl | 19b | I | 80 | Pa₆:0.82 |  |
|  | 19b | Boc—Val—Leu—Lys(Cbo)—4-ANMP | 19a | C/E | 78 | P₁:0.71 |  |
|  | 19a | Boc—Leu—Lys(Cbo)—4-ANMP | 18a | C/D | 90 | P₁:0.62 |  |
| XX |  | Boc—Gly—Pro—Lys—Isl.HCl | 20a | I | 48 | M₃:0.81 | −78.0° |
|  | 20a | Boc—Gly—Pro—Lys—4-ANMP.AcOH | 18c | G | 96 |  |  |
| XXI |  | Boc—Val—Leu—Lys—Isl.HCl | 21a | I | 41 | Pa₆:0.38 | −61.9° |
|  | 21a | Boc—Val—Leu—Lys—4-ANMP.AcOH | 19b | G |  |  |  |
| XXII |  | H—D-Leu—Ser—Arg—Isl.2 HCl | 22e | C | 70 | A:0.30 | −40° |
|  | 22e | Boc—D-Leu—Ser—Arg—Isl.AcOH | 22d | I | 77 | Pa₆:0.34 |  |
|  | 22d | Boc—D-Leu—Ser—Arg—4-ANMP.AcOH | 22c | G | 73 |  |  |
|  | 22c | Boc—D-Leu—Ser(OBzl)—Arg(NO₂)—4-ANMP | 22b | E | 87 | P₁:0.41 |  |
|  | 22b | H—Ser(OBzl)—Arg(NO₂)—4-ANMP.HCl | 22a | C | 84 | Pa₆:0.22 |  |
|  | 22a | Boc—Ser(OBzl)—Arg(NO₂)—4-ANMP | 1a | B/E | 80 | P₁:0.43 |  |
| XXIII |  | Tos—Phe—Pro—Arg—Isl.HCl | XII | F2 | 41 | A:0.48 | −68.3° |
| XXIV |  | H—D-Arg—Val—Tyr—Isl.2 HCl | 24e | I | 47 | A:0.32 | −11.7° |
|  | 24e | H—D-Arg—Val—Tyr—4-ANMP.2 AcOH | 24d | H | 84 | A:0.33 |  |
|  | 24d | H—D-Arg(NO₂)—Val—Tyr—4-ANMP.HCl | 24c | B | 80 | A:0.40 |  |
|  | 24c | α-Boc—D-Arg(NO₂)—Val—Tyr(OBzl)—4-ANMP | 24b | E | 74 | A:0.88 |  |
|  | 24b | H—Tyr(OBzl)—4-ANMP.TFA | 24a | C | 93 | Pa₆:0.60 |  |
|  | 24a | Boc—Tyr(OBzl)—4-ANMP |  | A |  | P₁:0.77 |  |
| XXV |  | Cbo—Gly—Gly—Arg—Lum.AcOH | 25b | I | 55 | A:0.37 | −20.6° |
|  | 25b | Cbo—Gly—Gly—Arg—3-ANMP.AcOH | 25a | D |  | A:0.43 |  |
|  | 25a | H—Arg—3-ANMP.2 AcOH | 13a | G |  | A:0.26 |  |
| XXVI |  | Suc—Ala—Pro—Ala—Isl | 26c | I | 53 | Pa₆:0.33 | −153.8° |
|  | 26c | Suc—Ala—Pro—Ala—4-ANMP | 26b | B/Fl | 85 | A:0.51 |  |
|  | 26b | Cbo—Ala—Pro—Ala—4-ANMP | 26a | B/E | 84 | P₁:0.60 |  |
|  | 26a | Cbo—Ala—4-ANMP |  | A | 81 | P₁:0.57 |  |
| XXVII |  | Ac—Ala—Pro—Val—Isl | 27c | I | 47 | Pa₆:0.68 | −164.2° |
|  | 27c | Ac—Ala—Pro—Val—4-ANMP | 27b | B/Fl | 92 | P₁:0.29 |  |

TABLE-continued

| End prod. | Intermediary prod. | Formula | Starting material | Synthesis | Yield | TLC system $R_f$ | $(\alpha)$ |
|---|---|---|---|---|---|---|---|
| | 27b | Cbo—Ala—Pro—Val—4-ANMP | 27a | B/E | 83 | $P_1$:0.63 | |
| | 27a | Cbo—Val—4-ANMP | | A | 68 | $P_1$:0.67 | |
| XXVIII | | Glt—Ala—Pro—Phe—Isl | 28c | I | 58 | $Pa_6$:0.61 | $-60.2°$ |
| | 28c | Glt—Ala—Pro—Phe—4-ANMP | 28b | B/Fl | 82 | $Pa_6$:0.77 | (i MeOH) |
| | 28b | Cbo—Ala—Pro—Phe—4-ANMP | 28a | B/E | 83 | $P_1$:0.75 | |
| | 28a | Cbo—Phe—4-ANMP | | A | 86 | $P_1$:0.67 | |

III. Determination of Protease Activity

Procedure

In a first step, the sample to be assayed for protease activity is allowed to react with the substrate. For this purpose, the buffer type, pH value, ionic strength and temperature should be decided on to warrant optimal reaction conditions for the enzyme in question. Thus the optimum activity for serine proteases within coagulation and fibrinolysis systems, as also trypsin, chymotrypsin, acrosine, elastase, urokinase, the streptokinase-plasminogen complex, plasminogen activators, Cl-esterase and its sub-components Clr and Cls as well as of the endotoxin-activated protease of the horseshoe crab lies within the pH range of 6.5 to 9.5. The ionic strength should be 0.05 to 0.40 and the temperature normally 25° to 37° C. All these proteases are determinable with substrates according to the invention.

The substrate concentration may be chosen in accordance with the degree of sensitivity required for the determination and depending on the preferred value in relation to the $K_m$-value. When extremely low protease activities are to be determined, that is, values approaching the lower limit of detection, blank values should be determined as in the case of pNA and MCA substrates. The usual substrate concentrations of the substrate-enzyme solution are $10^{-3}$ to $10^{-5}$M. A stock solution of the substrate is prepared in water or buffer; with sparingly soluble substrates organic solvents are to be used, such as ethanol, dimethylsulphoxide, dimethyl formamide or dimethylacetamide.

Depending on the degree of protease activity and substrate concentration, the reaction time usually is 0.5 to 5 minutes. With considerably longer reaction times, it is important that the spontaneous hydrolysis of the substrate is very slow. The reaction is stopped by adding either acid or base to produce a change in pH great enough to discontinue further protease activity which usually happens at pH values lower than 5 or higher than 11.

The amount of released marker is then determined by a reaction as described in the foregoing. Any one of various reagents mentioned above may be used, and the volumes may vary.

The following examples describe test conditions under which linear relations were obtained between protease activity and appliance responses in the oxidation reactions.

A number of various oxidation systems have been used, as, for instance, (a) substrate-enzyme solution (see example below): 10–50 $\mu$l
(b) 0.05M NaOH in water: 250–750 $\mu$l
(c) 5 to 10 $\mu$M hematin in 0.1M $Na_2CO_3$ in water: 20–100 $\mu$l
(d) 0.1 to 0.5M $H_2O_2$ in water: 20–100 $\mu$l The pH-regulating solution (b) is adapted to the applied catalyst/oxidation promoting compound (c). The following modifications were used:

(b) phosphate buffer pH 11.6 and (c) hematin as above
(b) NaOH as above and (c) catalase 30,000 units per ml of water
(b) 0.08M $Na_2CO_3$ pH 11.2 and (c) Microperoxidase (Sigma, U.S.A. Prod. No. M 6756, 0.4 mg/ml 10 mM tris buffer and HCl, pH 7.4, diluted 50 times with 50 mM borate buffer, pH 8.4)
(b) 50 mM borate buffer pH 8.4 and (c) Microperoxidase.

Instead of using the basic environment of the oxidation system to stop protease activity, 0.1 to 1.0 parts by volume of 20 to 100% acetic acid can be added to the enzyme-substrate solution. The content of acetic acid does not interfere with the pH of the oxidation solution.

Thus, determinations can be made with minute volumes (10–50 $\mu$l) of substrate-enzyme solution. The optimum volume (300 to 1,000 $\mu$l) of oxidation solution allowable for the used appliance is chosen.

Test 1

(a) 50 $\mu$l $10^{-4}$ Boc-Val-Leu-Lys-Isl.HCl (XXI) in a tris buffer pH 8.3, I=0.3 after being kept at 25° C. for varying lengths of time for observation of spontaneous hydrolysis of substrate in typical protease determination environment
(b) 700 $\mu$l 50 mM NaOH
(c) 20 $\mu$l 10 mM hemine
(d) 100 $\mu$l 80 mM $H_2O_2$ Result: Spontaneous hydrolysis 0.03% per hour, that is, after one hour, $3 \cdot 10^{-9}$M isoluminol had been liberated, thus, the substrate is very stable.

Test 2

(a) is 50 $\mu$l of either of the following:
$10^{-4}$M Boc-Val-Leu-Lys-Isl.HCl (XXI) substrate according to the above plus $10^{-5}$–$10^{-10}$M isoluminol
$10^{-5}$M Boc-Val-Leu-Lys-Isl.HCl (XXI) substrate according to the above plus $10^{-5}$–$10^{-10}$M isoluminol (b)–(d) as in Test 1.

Result: The appliance response is in rectilinear proportion to the amount of isoluminol; in the lowest concentration range—$10^{-7}$–$10^{-9}$ and $10^{-8}$–$10^{-9}$, respectively—the best results are obtained after the usual corrections for background contributions of the substrate. $1 \cdot 10^{-9}$M can be exactly determined. Isoluminol causes an appliance response 2,500 times larger than that of the substrate at the corresponding concentration, that is, the background is 0.04%.

Tests 3 to 7 are examples of protease activity determinations.

Test 3

Urokinase and pGlu-Gly-Arg-Isl.HCl (VI)
Substrate-enzyme solution:
Tris buffer pH 9.0 I=0.05: 800 μl
Urokinase (AB Leo, Sweden) 2.5-20 Plough units per: 100 μl
Substrate $10^{-3}$M in water: 200 μl
Reaction time 5 minutes, temperature 37° C.
20% AcOH: 100 μl
50 μl of the solution is used for determination of the amount of isoluminol according to Test 1.

Test 4

Thrombin and Tos-Phe-Pro-Arg-Isl.HCl (XXIII)
Substrate-enzyme solution:
Tris buffer pH 8.3 I=0.15: 800 μl
Thrombin (Ortho, U.S.A.) 0.02-0.32 NIH-units per: 100 μl
Substrate $10^{-3}$M in water: 100 μl
Reaction time 1 minute, temperature 37° C.
20% AcOH: 100 μl
50 μl of the solution is used for determination of the amount of isoluminol according to Test 1.

Test 5

Factor Xa and Boc-Ile-Glu(NC$_5$H$_{10}$)-Gly-Arg-Isl.HCl (VIII)
Substrate-enzyme solution:
Tris buffer pH 8.3 I=0.25: 800 μl
Factor Xa (Diagnostic Reagents, England) 0.05-0.8 units (U) per: 100 μl
Substrate $10^{-3}$M in water: 200 μl
Reaction time 1 minute, temperature 37° C.
20% AcOH:
50 μl of the solution is used for determination of isoluminol according to Test 1.

Test 6

Plasmin and Boc-Val-Leu-Lys-Isl.HCl (XXI)
Substrate-enzyme solution:
Tris buffer pH 7.4, I=0.15: 700 μl
Plasmin (Kabi, Sweden) 0.00125-0.02 U per: 100 μl
Substrate $10^{-3}$ in water: 300 μl
Reaction time 1 minute, temperature 37° C.
20% AcOH: 100 μl
50 μl of the solution is used for determination of isoluminol according to Test 1.

Test 7

Trypsin and substrates No. V, VI, VIII, X, XI, XII, XIII, XV, XVI and XX
Substrate-enzyme solution:
$1\cdot10^{-5}$–$1\cdot10^{-9}$M trypsin in 1 mM HCl: 30 μl
Substrate $1$–$1.5\cdot10^{-3}$M in water: 60 μl
Tris buffer 10 mM pH 8.3: 210 μl
Reaction time 5 minutes at room temperature.
25 μl of the substrate-enzyme solution is used for determination of the amount of marker of the system.
0.8 mM Na$_2$CO$_3$ pH 11.2: 240 μl
Microperoxidase: 20 μl
90 mM H$_2$O$_2$ in water: 20 μl The results from Tests 3 to 7 show a rectilinear relation between appliance response and protease volume. The amount of released marker per time unit is of the magnitude expected on the basis of known data on corresponding substrate structures with chromogenic and fluorogenic markers.

We claim:

1. Peptide derivatives being acyl derivatives of luminol(5-amino-2,3-dihydro-1,4-phthalazinedione) or isoluminol (6-amino-2,3-dihydro-1,4-phthalazinedione) wherein the acyl residue is an amino acid, or amino acid sequence, with 2 to 4 amino acid residues, coupled with an amide bond, and wherein the α-amino group is either free or acylated.

2. Peptide derivatives according to claim 1, wherein the C-terminal amino acid is L-arginine, L-lysine, L-alanine, L-phenylalanine, L-tyrosine, L-valine or L-proline.

3. Peptide derivatives, according to claim 1, wherein the amino acids are selected from the group of straight or branched aliphatic amino acids with 2-6 carbon atoms, hydroxy substituted derivatives thereof, cyclic imino acids with 4-6 carbon atoms, arginine, lysine, pyroglutaminic acid, glutaminic acid, aspartic acid, ester derivative of the γ-carboxy group of glutaminic acid or of aspartic acid, or amido derivative of β-carboxy group of glutaminic acid or of aspartic acid.

4. Peptide derivatives, according to claim 1, wherein the N-terminal amino acid group is in the D-form with the α-amino group being either free or a protonized acid addition salt.

5. Peptide derivatives, according to claim 2, wherein the 1-3 N-terminal amino acids of the peptide derivative are selected from the group of Gly, Ala, Val, Leu, Ile, Pro, Pip, Phe, Tyr, Arg, Lys, Ser, Thr, pGlu, Glu or Asp, or esters with 1-4 carbon atoms of Glu or Asp, Asn or Gln or substituted amides with substituents containing 1-5 carbon atoms of Asn or Gln.

6. Peptide derivatives according to claim 1 wherein the N-terminal α-amino group of the amino acid or peptide derivative is acylated with Bz, Cbo, pNO$_2$—Bz, pNO$_2$—Cbo, Boc, Ac, trifluoroacetyl, Glt, Suc or Tos.

7. Peptide derivatives characterized by the general formula

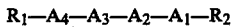

wherein
R$_1$=H, or acyl
A$_4$=Val, Ile, Ala, Gly, or nil,
A$_3$=Pro, Phe, Gly, Val, pGlu, Leu, Glu(pip), Ala, Glu, Glu(OMe), Arg, Ile, Tyr, or nil,
A$_2$=Phe, Pro, Leu, Ser, Gly, Val, Ala or nil,
A$_1$=Arg, Lys, Tyr, Phe, Ala, Val, Pro
R$_2$=luminol (5-amino-2,3-dihydro-1,4-phthalazinedione), isoluminol (6-amino-2,3-dihydro-1,4-phthalazinedione)
and wherein the N-terminal amino acid of the peptide sequence appears in L- or D-form.

8. Peptide derivative, according to claim 1, which is Boc-Val-Leu-Lys-Isl.

9. Peptide derivative, according to claim 1, which is pGlu-Gly-Arg-Isl.

10. Peptide derivative, according to claim 1, which is Tos-Phe-Pro-Arg-Isl.

11. Peptide derivative, according to claim 1, which is Boc-Ile-Glu(NC$_5$H$_{10}$)-Gly-Arg-Isl.

12. Peptide derivative, according to claim 1, which is H-D-Val-Leu-ARg-Isl.

13. Peptide derivative, according to claim 1, which is Cbo-Phe-Arg-Isl.

14. The peptide derivative of claim 7 wherein said cycle is selected from the group of Bz, pNO$_2$Bz, Boc, Cbo, pNO$_2$Cbo, Ac, Suc, Glt, or Tos.

15. Peptide derivative according to claim 1 which is Boc-Phe-Pro-Arg-Isl.

16. Peptide derivative according to claim 1 which is H-Phe-Pro-Arg-Isl.

17. Peptide derivative according to claim 1 which is Bz-Arg-Lum.

18. Peptide derivative according to claim 1 which is Bz-Arg-Isl.

19. Peptide derivative according to claim 1 which is pNO$_2$-Bz-Arg-Isl.

20. Peptide derivative according to claim 1 which is Boc-Gly-Pro-Lys-Isl.

21. A method for the determination of the activity of proteases which comprises contacting the substance for which said determination is desired with a peptide derivative being an acyl derivative of luminol (5-amino-2,3-dihydro-1,4-phthalazinedione) or isoluminol (6-amino-2,3-dihydro-1,4-phthalazinedione) wherein the acyl residue is an amino acid, or amino acid sequence, with 2 to 4 amino acid residues, coupled with an amide bond, and wherein the α-amino group is either free or acylated; adding an oxidizer after contacting said substance with said peptide derivative; and then measuring the quantity of light emitted.

22. The method of claim 21 wherein the C-terminal amino acid of said peptide derivative is L-arginine, L-lysine, L-alanine, L-phenylalanine, L-tyrosine, L-valine, or L-proline.

23. The method of claim 21 wherein the amino acids of said peptide derivative are selected from the group of straight or branched aliphatic amino acids with 2-6 carbon atoms, hydroxy substituted derivatives thereof, cyclic imino acids with 4-6 carbon atoms, arginine, lysine, pyroglutaminic acid, glutaminic acid, aspartic acid, ester derivative of the γ-carboxy group of glutaminic acid, or of aspartic acid, or amido derivatives of β-carboxy group of glutaminic acid or of aspartic acid.

24. The method of claim 21 wherein the N-terminal amino acid group of said peptide derivative is in the D-form with the α-amino group being either free or a protonized acid addition salt.

25. The method of claim 22 wherein the 1-3 N-terminal amino acids of the peptide derivative are selected from the group of Gly, Ala, Val, Leu, Ile, Pro, Pip, Phe, Tyr, Arg, Lys, Ser, Thr, pGlu, Glu or Asp, or esters with 1-4 carbon atoms of Glu or Asp, Asn or Gln, or substituted amides with substituents containing 1-5 carbon atoms of Asn or Gln.

26. The method of claim 21 wherein the N-terminal α-amino group of the amino acid or peptide derivative is acylated with Bz, Cbo, pNO$_2$—Bz, pNO$_2$—Cbo, Boc, Ac, trifluoroacetyl, Glt, Suc, or Tos.

27. The method of claim 21 wherein said peptide derivative has the formula:

$$R_1-A_4-A_3-A_2-A_1-R_2$$

where
- $R_1$ = H, or acyl
- $A_4$ = Val, Ile, Ala, Gly, or nil
- $A_3$ = Pro, Phe, Gly, Val, pGlu,, Leu, Glu (pip), Ala, Glu, Glu (OMe), Arg, Ile, Tyr, or nil
- $A_2$ = Phe, Pro, Leu, Ser, Gly, Val, Ala, or nil
- $A_1$ = Arg, Lys, Tyr, Phe, Ala, Val, Pro
- $R_2$ = luminol (5-amino-2,3-dihydro-1,4-phthalazinedione), isoluminol (6-amino-2,3-dihydro-1,4-phthalazinedione) and where the N-terminal amino acid of the peptide sequence appars in L- or D-form.

28. The method of claim 27 wherein said acyl is selected from the group of Bz, pNO$_2$—Bz, Boc, Cbo, pNO$_2$—Cbo, Ac, Suc, Glt, or Tos.

29. The method of claim 21 wherein said peptide derivative is selected from the group of Boc-Val-Leu-Lys-Isl, pGlu-Gly-Arg-Isl, Tos-Phe-Pro-Arg-Isl, Boc-Ile-Glu(NC$_5$H$_{10}$)-Gly-Arg-Isl, H-D-Val-Leu-Arg-Isl, or Cbo-Phe-Arg-Isl.

* * * * *